United States Patent [19]

Kim et al.

[11] Patent Number: 4,965,396

[45] Date of Patent: Oct. 23, 1990

[54] NITROBENZOYL-3-CYCLO-PROPYLAMINOACRYLATES AND A PROCESS FOR THE PREPARATION THEREOF

[75] Inventors: You Seung Kim; Sang Woo Park; Jea Cheol Kim, all of Seoul, Rep. of Korea

[73] Assignee: Korea Advanced Institute of Science and Technology, Seoul, Rep. of Korea

[21] Appl. No.: 321,971

[22] Filed: Mar. 10, 1989

[30] Foreign Application Priority Data

Jun. 17, 1988 [KR] Rep. of Korea .................. 7341/1988

[51] Int. Cl.$^5$ .......................................... C07C 205/00
[52] U.S. Cl. ...................................................... 560/21
[58] Field of Search ....................................... 560/21,43

[56] References Cited

U.S. PATENT DOCUMENTS

| | | | |
|---|---|---|---|
| 4,695,646 | 9/1987 | Maurer et al. | 560/43 |
| 4,699,992 | 10/1987 | Grohe | 560/21 |
| 4,711,898 | 12/1987 | Enomoto et al. | 560/43 |

*Primary Examiner*—Bruce Gray
*Attorney, Agent, or Firm*—Darby & Darby

[57] ABSTRACT

Nitrobenzoyl-3-cyclopropylaminoacrylates are prepared by two stage reaction: (a) The first stage is the synthesis of nitrobenzoyl-3-alkoxyacrylates from nitrobenzoylester compound and alkylorthoformate in organic acid solvent. (b) The second stage is the synthesis of nitrobenzoyl-3-cyclo propylamino acrylate from nitrobenzoyl-3-alkoxyacrylates and cyclopropylamine.

1 Claim, No Drawings

NITROBENZOYL-3-CYCLOPROPYLAMINOA-CRYLATES AND A PROCESS FOR THE PREPARATION THEREOF

BACKGROUND OF THE INVENTION

The present invention relates to nitrobenzoyl-3-cyclopropylaminoacrylates of the formula (I) and the preparation process thereof.

(I) [structure: 4-fluoro, X-substituted nitrobenzoyl connected to C(=O)-C(=CH-NH-cyclopropyl)-C(=O)OR]

wherein
R = methyl, ethyl or propyl
X = halogen (chloro, fluoro or bromo).

Nitrobenzoyl-3-cyclopropylaminoacrylates of the formula (I) are the good intermediate for the preparation of quinolon derivatives (IV) with strong sterilization effect for bacteria (antibacterial agent).

(IV) [structure: fluoro, X-substituted quinolone with COOH and N-cyclopropyl]

wherein
X = halogen (chloro, fluoro or bromo).

The process for the preparation of nitrobenzoyl-3cyclopropylaminoacrylates of the formula (I) consists of two stage reactions:

The first stage is to prepare nitrobenzoyl-3-alkoxyacrylates of the formula (III), which can be obtained by reacting nitrobenzoylester compound of the formula (II) with alkylorthoformate in organic acid solvent and the second one is to prepare nitrobenzoyl-3-cyclopropylaminoacrylates of the formula (I), which can be obtained by reacting nitrobenzoyl-3-alkoxyacrylates of the formula (III) and cyclopropylamine.

(II) [structure: F, X-substituted nitrobenzoyl-CH2-C(=O)OR]

wherein
R = methyl, ethyl or propyl
X = halogen (chloro, bromo or fluoro)

(III) [structure: F, X-substituted nitrobenzoyl-C(=C(OR')H)-C(=O)OR]

wherein
R = methyl, ethyl or propyl
X = halogen (chloro, fluoro or bromo)
R' = methyl, ethyl.

DETAILED DESCRIPTION OF THE INVENTION

The detailed preparation method of nitrobenzoylester compounds of the formula (II) from dihalobenzene is described in the previous patent on "Benzoylacetic ester derivatives and their preparation process."

The nitrobenzoyl-3-alkoxyacrylates of the formula (III) can be obtained by refluxing the acetic acid anhydrous solution of nitrobenzoyl ester compound of the formula (II) and ethyl or methylorthoformate for 1 to 5 hours.

Wherein the equivalent ratio between alkylorthoformate and nitrobenzoylester compound of the formula (II) is preferably from 1.2 to 1.5.

Nitrobenzoyl-3-cyclopropylaminoacrylates of the formula (I) are prepared by adding cyclopropylamine to nitrobenzoyl-3-alkoxyacrylates of the formula (III), then stirring 18°–30° C. for 1 hour wherein the equivalent ratio between cyclopropylamine and nitrobenzoyl-3-alkoxyacrylate is preferably from 1.2 to 1.5.

In order to describe this invention more precisely, we have an example as follows;

This example is the synthetic process of nitrobenzoyl-3-cyclopropylaminoacrylate of the formula (I) from the compound of the formula (II).

In this case, R = ethyl and X = chloro in formula (II), R' = methyl in formula (III) and R = ethyl and X = chloro in formula (I) are confined.

[structure: 4-F, 5-Cl nitrobenzoyl-CH2-C(=O)OC2H5]  $(CH_3O)_3CH$ / acetic acid anhydrous →

Corresponds to (II)

[structure: 4-F, 5-Cl nitrobenzoyl-C(=CH-OCH3)-C(=O)OC2H5]

Corresponds to (III)

$H_2N$—◁
↓

-continued

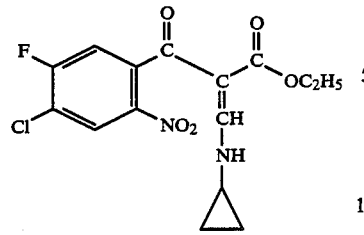

Corresponds to (I)

The present invention will now be descirbed in detail with reference to the following examples.

EXAMPLE 1 ethyl (4,5-difluoro-2-nitrobenzoyl)-3-ethoxyacrylate (III, X=fluoro, R=ethyl)

To 3 ml of acetic acid anhydrous were added 3 g (0.01 mol) of ethyl 4,5-difluoro-2-nitrobenzoylacetate and 2.44 g (0.016 mol) of ethylorthoformate.

The reactants were refluxed for about 2 hours.

The reaction product after removing the solvent under reduced pressure of 10 mmHg was directly used for the next reaction without any purification.

EXAMPLE 2 ethyl (4,5-difluoro-2-nitrobenzoyl)-3-cyclopropylaminoacrylate (I, X=fluoro, R=ethyl)

A solution of 0.65 g (0.012 mol) of cyclopropylamine was added dropwisely to the compound of the formula (III), wherein X is fluoro and R is ethyl, at 0° C. prepared in Example 1.

After stirring the reactants at 20±2° C. for 15 min, 2.95 g (yield 87%, wt %), of solid product could be obtained after filtration and drying process.

mp: 123°-125° C.

NMR (CDCl3)ppm: 11.0 (1H, s), 8.76 (1H, d), 7.95-8.23 (1H, q), 6.92-7.33 (1H, q), 3.83-4.23 (2H, q), 2 m76-3.33 (1H, m), 0.79-1.03 (7H, m).

IR(KBr): 1685, 1620, 1530, 1410, 1350 cm$^{-1}$,

CHN analysis for $C_{15}H_{14}F_2N_2O_5$; calculated value: C 63.82, H 6.78, N 8.23. observed value: C 63.79, H 6.90, N 8.14.

EXAMPLE 3 ethyl-(4-chloro-5-fluoro-2-nitrobenzoyl)-3-ethoxyacrylate (III, X=chloro, R=ethyl)

The procedure of example 1 was repeated while varying the starting compound and the product was obtained. The starting compound was ethyl-4-chloro-5-fluoro-2-nitrobenzoyl acetate (II, X=chloro, R=ethyl)

EXAMPLE 4 ethyl-(4-chloro-5-fluoro-2-nitrobenzoyl)-3-cyclopropylamino acrylate (I, X=chloro, R=ethyl)

The procedure of example 2 was repeated while varying the starting compound and the solid products was obtained (yield 71%, wt %).

The starting compound was the compound of the formula III wherein X is chloro and R is ethyl.

NMR(CDCl3)ppm: 8.15-8.60 (2H, m), 7.20 (1H, d), 3.80-4.20 (2H, q), 2.75-3.35 (1H, m), 0.77-1.01 (7H, m).

What is claimed is:

1. A compound of nitrobenzoyl-3-cyclopropylaminoacrylate of the formula (I)

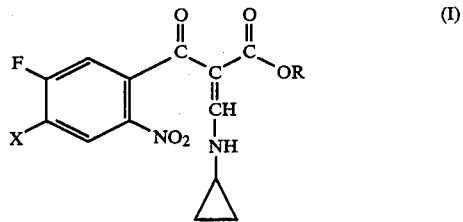

wherein R is ethyl and X is chloro or fluoro.

* * * * *